US006998265B2

(12) United States Patent
Banes

(10) Patent No.: US 6,998,265 B2
(45) Date of Patent: Feb. 14, 2006

(54) METHOD AND APPARATUS TO GROW AND MECHANICALLY CONDITION CELL CULTURES

(75) Inventor: Albert J. Banes, Hillsborough, NC (US)

(73) Assignee: MedTrain Technologies, LLC, Hillsborough, NC (US)

( * ) Notice: Subject to any disclaimer, the term of this patent is extended or adjusted under 35 U.S.C. 154(b) by 626 days.

(21) Appl. No.: 10/296,742

(22) PCT Filed: Dec. 10, 2001

(86) PCT No.: PCT/US01/47745

§ 371 (c)(1),
(2), (4) Date: Nov. 26, 2002

(87) PCT Pub. No.: WO02/46365

PCT Pub. Date: Jun. 13, 2002

(65) Prior Publication Data

US 2004/0014205 A1 Jan. 22, 2004

Related U.S. Application Data

(60) Provisional application No. 60/254,144, filed on Dec. 8, 2000.

(51) Int. Cl.
*C12N 5/00* (2006.01)
*C12M 3/00* (2006.01)
(52) U.S. Cl. .................. 435/401; 435/395; 435/305.1; 435/305.2; 623/915
(58) Field of Classification Search ................ 435/1.1, 435/395, 397, 401, 402, 288.3, 288.4, 297.5, 435/305.1, 305.2, 305.3, 305.4; 623/915
See application file for complete search history.

(56) References Cited

U.S. PATENT DOCUMENTS

| 4,839,280 A | 6/1989 | Banes |
| 4,851,354 A | 7/1989 | Winston et al. |
| 5,153,136 A | 10/1992 | Vandenburgh |
| 5,348,879 A | 9/1994 | Shapiro et al. |
| 5,518,909 A | 5/1996 | Banes |
| 5,686,303 A | 11/1997 | Korman |
| 6,037,141 A | 3/2000 | Banes |
| 6,048,723 A | 4/2000 | Banes |
| 6,207,451 B1 * | 3/2001 | Dennis et al. .............. 435/325 |
| 6,218,178 B1 | 4/2001 | Banes |

\* cited by examiner

*Primary Examiner*—William H. Beisner
(74) *Attorney, Agent, or Firm*—The Webb Law Firm

(57) ABSTRACT

An apparatus (10) to grow cell cultures includes an anchor (14) potted to a flexible membrane (12) and an anchor stem (16) to which cells attach. A jig (18) having a trough (46) and at least one passage (52) is positioned adjacent the flexable membrane (12). A method for growing and mechanically conditioning three-dimensional cell constructs begins by drawing the flexible membrane (12) and the anchor stem (14) into the trough (46) by means (20) for flexing the flexible membrane (12) (step 114). Cells are supplied (step 116) and allowed to attach to the anchor stem (16) (step 118). The flexible membrane (12) is released from within the trough (46) (step 120), resulting in a three-dimensional structure (34) of cells attached to the anchor stem (16). The cells grow into the three-dimensional construct (step 130). The structure (34) and/or the construct can be subjected to a regimen of strain for mechanical conditioning of the cells (step 132).

20 Claims, 8 Drawing Sheets

METHOD AND APPARATUS TO GROW AND MECHANICALLY CONDITION CELL CULTURES

This application claims the benefit of Provisional App. No. 60/254,144, filed Dec. 08/2000.

BACKGROUND OF THE INVENTION

1. Field of the Invention

The present invention is directed to tissue engineering and, more particularly, to creating a three dimensional construct of cells and mechanically conditioning the construct.

2. Description of Related Art

Connective tissue cells from muscle, bone, tendon, ligament, and cartilage respond to mechanical loading. Many types of devices have been developed to apply static or cyclic strain to cells. These devices include reciprocating arms clamped to a matrix substrate, weights placed upon cells grown on a distensible membrane, and a forcing frame in which cells on a distensible substrate are statically stretched.

A particular device, conceived by the present inventor, applies static or cyclic tension or compression to cultured cells grown on a deformable substrate. The deformation of the substrate is regulated by pressure controlled by a solenoid valve and a timer. In one embodiment of the device, a vacuum is used to downwardly deform a polystyrene surface on which tendon cells are attached. The cells respond by altering their synthesis of cytoskeletal proteins. This device evolved into a computer controlled device that provides regimens of strain having defined duration, frequency, and amplitude which are either static or cyclic. A culture plate that allows easy growth of cells on a flexible bottom culture plate is used with this device. This device is known as a Flexercell® Strain Unit (FSU) provided by Flexcell International Corporation. The FSU controls devices that provide regulated strain in the form of tension, compression, and fluid-induced shear stress to cells. These types of strain encompass the broad areas of strain types experienced by a multitude of cells in native environments of the body. This device created a new field of study known as cytomechanics and has provided a standard instrument and culture plate for broad use in the marketplace. For reference, see U.S. Pat. Nos. 6,218,178; 6,048,721; and 5,518,909.

Research by Flexcell International Corporation shows that cells that have been subjected to a particular regimen of cyclic strain followed by rest (for example, 1 Hz, 1% substrate elongation, 8 hours/day for 3 days) respond with an increased ability to attach and spread on a substrate and resist removal by fluid flow. Flexcell International Corporation calls this cell-based training response "mechanical conditioning". It is theorized that different training regimen will produce different training responses in cells, including the ability of cells to attach, spread, and adhere to a matrix; organize an oriented three dimensional matrix; express a native matrix; maintain a level of cell division; and in general, maintain a native phenotype that is biochemically and biomechanically normal.

Cells in tissue environments in the body are present in three dimensional matrices. These matrices have their own particular anatomy, material structure, and biomechanical properties. As a tissue develops, its cells require an appropriate degree of mechanical deformation, as well as nutrition supplied by either diffusion from extracellular fluids or by delivery of nutrients through the blood vascular system. In order to develop and utilize tissue-engineered, biocompatible materials that can sustain cell growth in vitro and withstand the rigors of the biomechanical environment, a proper structure design as well as means to provide nutrient availability must be created. The structure must: 1) support cell attachment and growth; 2) be easy to infiltrate with cells; 3) be biocompatible, that is of low immunogenicity or antigenicity if it is to be implanted in an animal or a human; 4) have a structure compatible with cell division followed by differentiation, matrix expression, and differentiated function; 5) have a structure that allows collection of a bioproduct and/or cells; 6) be chemically stable; 7) be easily obtained, formed, manufactured, and sterilized; and 8) be inexpensive.

SUMMARY OF THE INVENTION

It is an object of this invention to provide the instrumentation, technologies, and methodologies for mechanically conditioning cells in vitro to acquire a trained cell phenotype and stimulate cells to synthesize their own organized matrix in vitro or ex vivo so that: 1) an engineered construct of cells can be inserted into the body as a functional part of an organ or as a fully functional organ, and 2) cells can be prepared for seeding into their own matrix or a synthetic or biosynthetic matrix structure so that existing tissues in the body can be augmented or repaired.

The present invention includes methods and apparatus to grow and mechanically condition cell constructs, including sterile devices to incubate, nutrify, and mechanically, electrically, and/or biochemically condition cells, matrices, or constructs.

An apparatus to grow cell cultures according to the present invention includes a flexible membrane. An anchor is potted to a periphery of the flexible membrane. An anchor stem extends from the anchor and includes a free portion to which cells may attach. A jig is positioned adjacent to the flexible membrane. The jig includes a trough positioned next to the flexible membrane and at least one passage. A means for flexing the flexible membrane is also provided, such as a vacuum source in fluid communication with the at least one passage.

Preferably, the flexible membrane is the flexible membrane of a well-type culture plate. The well houses the flexible membrane, anchor, anchor stem, and jig. The jig is positioned to form a space between itself and the bottom of the well, for example, a gasketed membrane. The vacuum source is in fluid communication with the space which is, in turn, in fluid communication with the at least one passage.

The apparatus is used for growing and mechanically conditioning three-dimensional constructs of cell cultures. The flexible membrane and the anchor stem therewith are drawn into the trough by applying a vacuum from the vacuum source. Cells are supplied to the flexible membrane where the flexible membrane has been drawn into the trough. Once the cells attach to the anchor stem, the vacuum is extinguished and the flexible membrane is released from within the trough. The result is a three-dimensional structure of cells that is attached to the anchor stem. The cells of the structure are allowed to grow into a three-dimensional construct.

The structure and/or the construct are subjected to a regimen of strain to mechanically condition the structure and/or the construct. The strain simulates strains encountered inside a body. The regimen of strain is applied using the vacuum source. By applying and extinguishing a vacuum, the flexible membrane is subjected to strain, thereby subjecting the cells on the flexible membrane to strain. The strain applied may be biaxial or uniaxial depending on the configuration of the jig.

The present invention may be used to grow and mechanically condition cells destined to become a construct of connective tissue such as skin, muscle, bone, intervertebral disc, tendon, ligament; a construct of non-connective tissue such as bowel, liver, pancreas, spleen, thymus; or a construct of an internal organ such as an eye, a reproductive organ, a lymph node, or other organs or parts thereof.

For example, endothelial cells or smooth muscle cells destined to be seeded into a vascular prosthesis comprising a blood vessel may be grown and mechanically conditioned to rapidly attach and spread on an engineered substrate and to resist detachment by forces applied in vivo, such as the strain of applied muscle force, reactive ground forces, vibration, or fluid flow.

As another example, cultured chondrocytes may be conditioned so that they express a matrix that can be integrated into a host tissue and withstand the rigors of compressive loading in articular cartilage in the knee, hip, or other joint.

The present invention may be used in core units in hospitals where cells from a patient can be collected, cultured, mechanically conditioned, and seeded directly into an organ needing repair or replacement or into matrices that would be implanted into an organ.

DETAILED DESCRIPTION OF THE PREFERRED EMBODIMENTS

Figure 1:
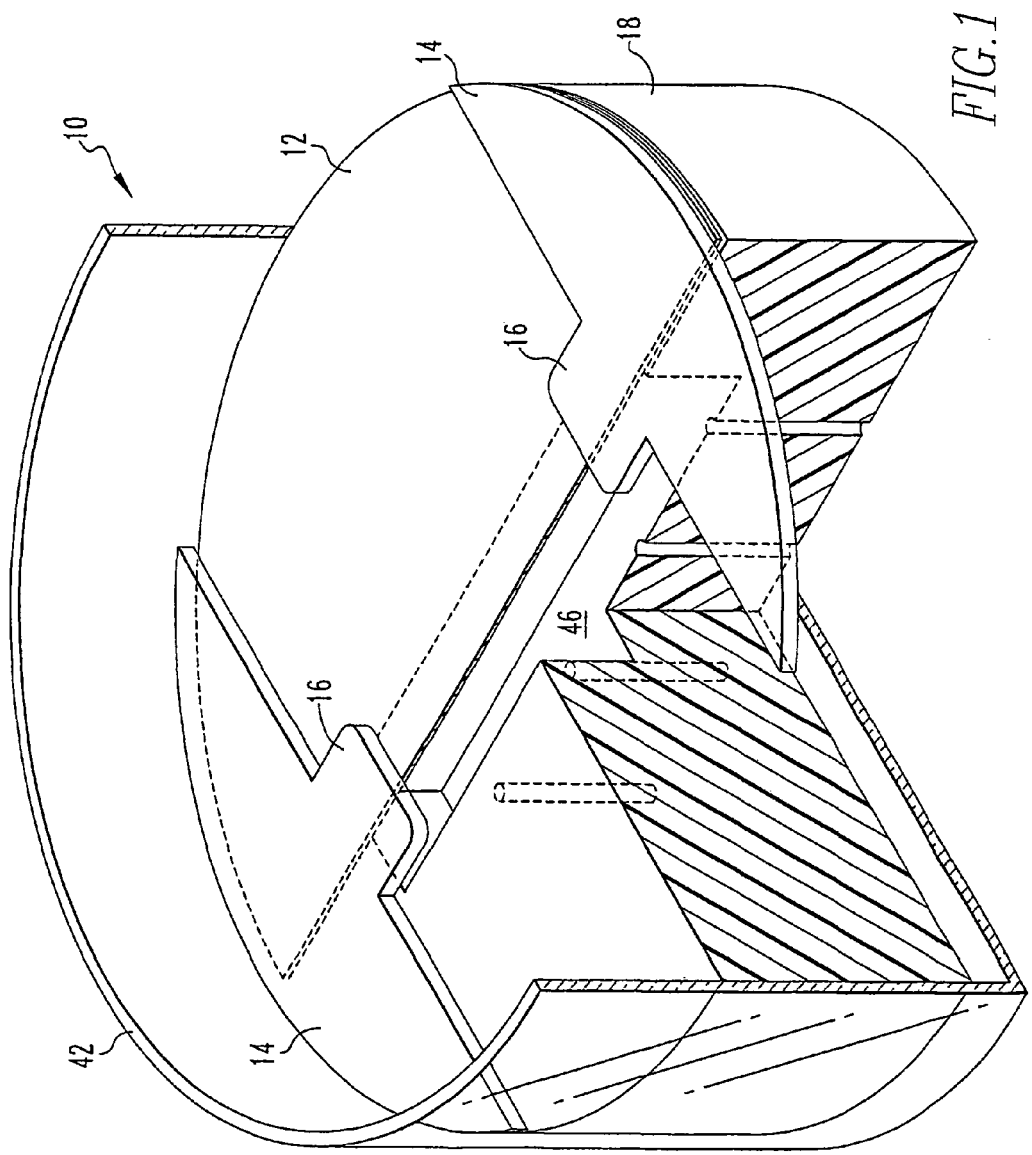
FIG. 1 is a front perspective view of an apparatus to grow and mechanically condition cell cultures according to the present invention.

A complete understanding of the invention will be obtained from the following description when taken in connection with the accompanying drawing figures wherein like reference characters identify like parts throughout.

For purposes of the description hereinafter, the terms "upper", "lower", "right", "left", "vertical", "horizontal", "top", "bottom", and derivatives thereof shall relate to the invention as it is oriented in the drawing figures. However, it is to be understood that the invention may assume various alternative variations and step sequences, except where expressly specified to the contrary. It is also to be understood that the specific devices and processes illustrated in the attached drawings, and described in the following specification, are simply exemplary embodiments of the invention. Hence, specific dimensions and other physical characteristics related to the embodiments disclosed herein are not to be considered as limiting.

Figure 2:
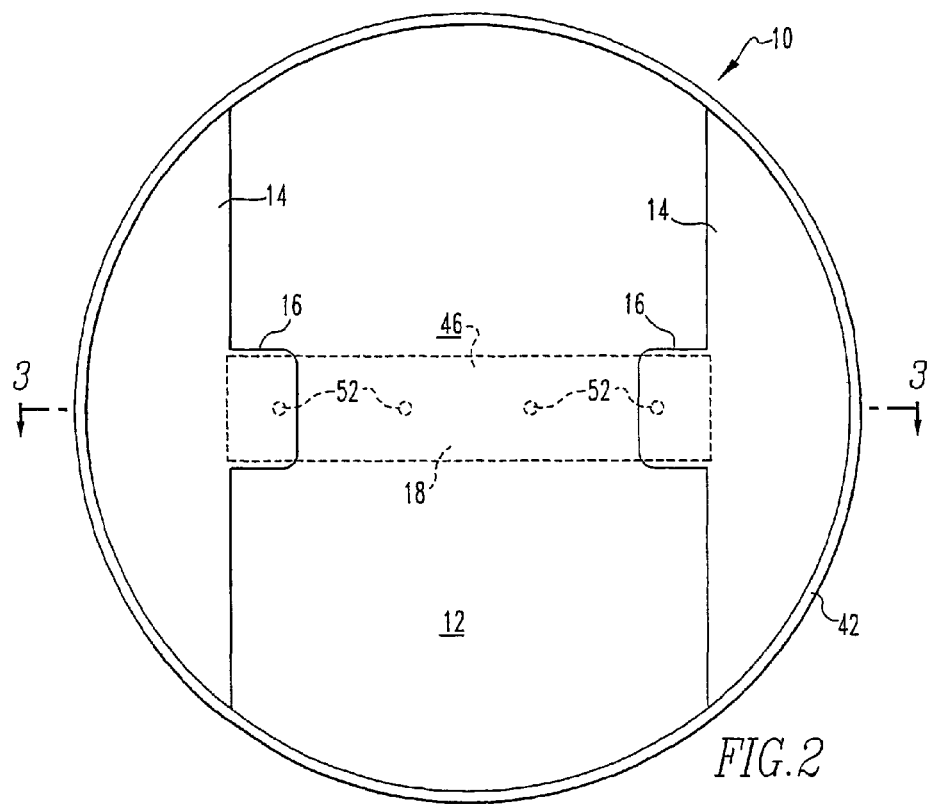
FIG. 2 is a top view of the apparatus shown in FIG. 1.
Figure 3:
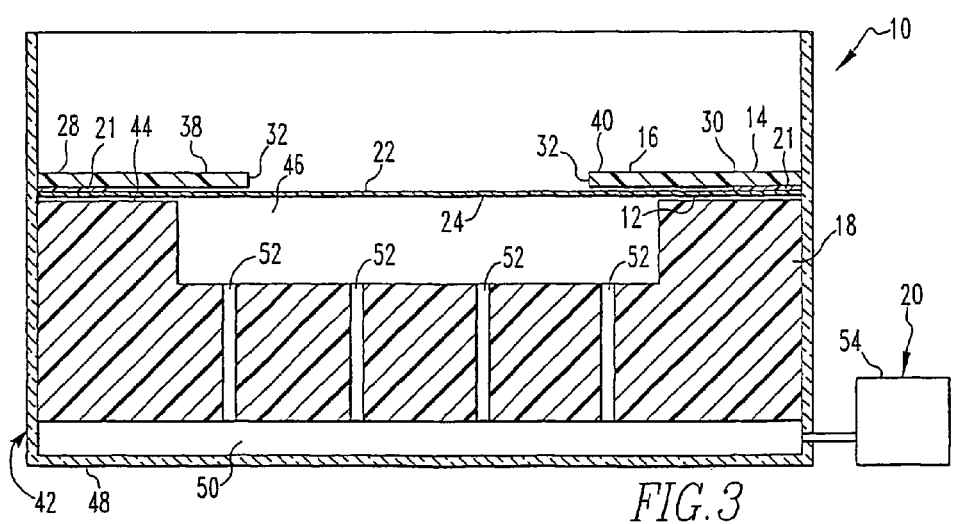
FIG. 3 is a section taken along line III—III in FIG. 2.

Referring to FIGS. 1–3, an apparatus 10 to grow cell cultures according to the present invention includes a flexible membrane 12, an anchor 14, an anchor stem 16, a jig 18, and means 20 for flexing the flexible membrane 12.

The flexible membrane 12 has a first or upper surface 22 and a second or lower surface 24. Preferably, the flexible membrane 12 is the flexible bottom of a well-type culture plate. A typical six-well culture plate would have six flexible membranes 12, one in each well 42. The flexible membrane 12 and the well 42 are preferably transparent. For example, the flexible membrane 12 may be the flexible bottom membrane in a BioFlex® Culture Plate well (by Flexcell International Corporation) which has not been treated with reagents to allow cells to adhere to it, as is typical.

The anchor 14 is attached at 21, or potted, to the first surface 22 of the flexible membrane 12. The anchor 14 may be attached to the flexible membrane 12 using a silicone rubber formulation or other like adhesive or bonding material. Preferably, the anchor 14 includes a first member 28 and a second member 30. Each of the first member 28 and the second member 30 are attached to the first surface 22 of the flexible membrane 12, preferably at diametrically opposed locations.

Figure 10:
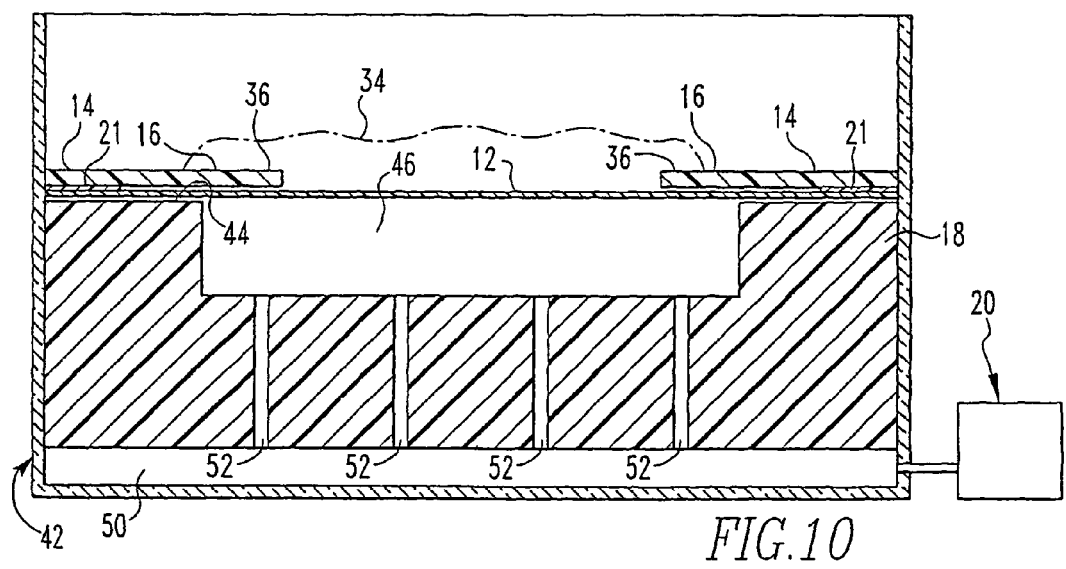
FIG. 10 is a section taken along line III—III in FIG. 2 and having a cell structure attached to a tissue segment.

The anchor stem 16 extends from the anchor 14 and is not potted to the flexible membrane 12. Thus, the anchor stem 16 has a free portion 32 to which cells can attach as a structure 34 (see FIG. 10) and grow into a construct. Similar to the anchor 14, the anchor stem 16 preferably includes a first section 38 and a second section 40 diametrically opposed to each other. The first section 38 of the anchor stem 16 extends from the first member 28 of the anchor 14, and the second section 40 of the anchor stem 16 extends from the second member 30 of the anchor 14. In this configuration, the cells attached to the opposed sections 38 and 40 of the anchor stem 16 will grow toward each other and, thereafter, intermingle to form a continuous construct.

Figure 4:
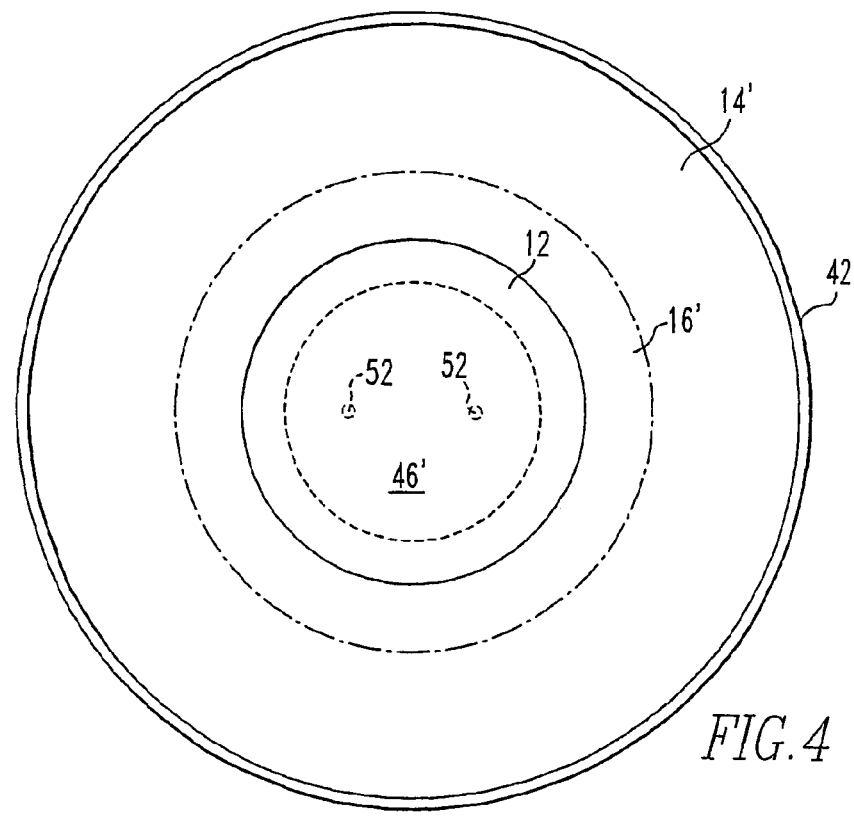
FIG. 4 is a top view of a second embodiment of an apparatus to grow and mechanically condition cell cultures according to the present invention.
Figure 5:
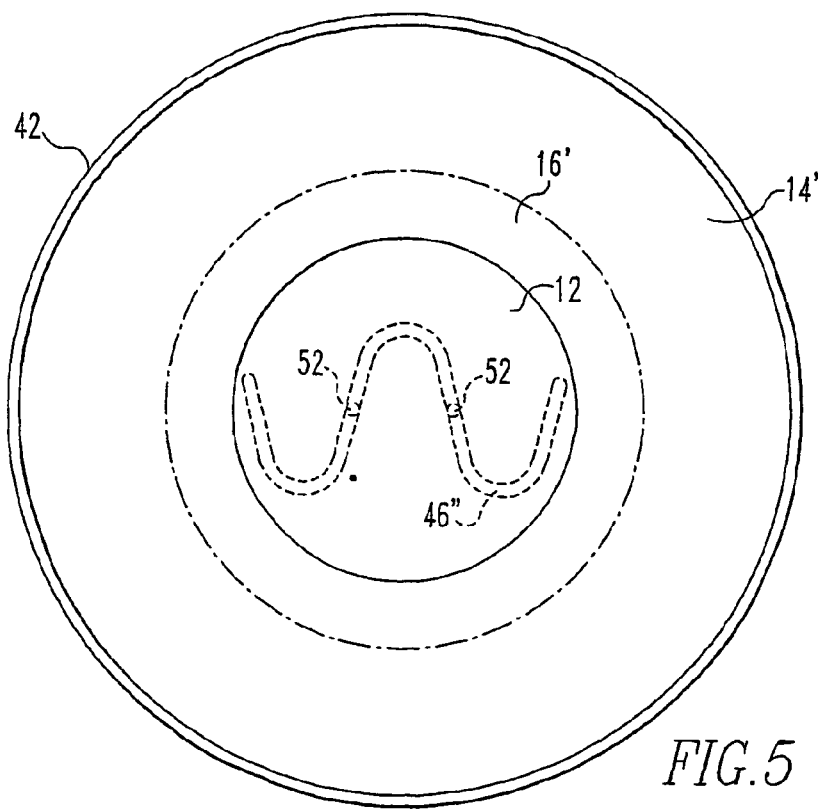
FIG. 5 is a top view of a third embodiment of an apparatus to grow and mechanically condition cell cultures according to the present invention.
Figure 6:
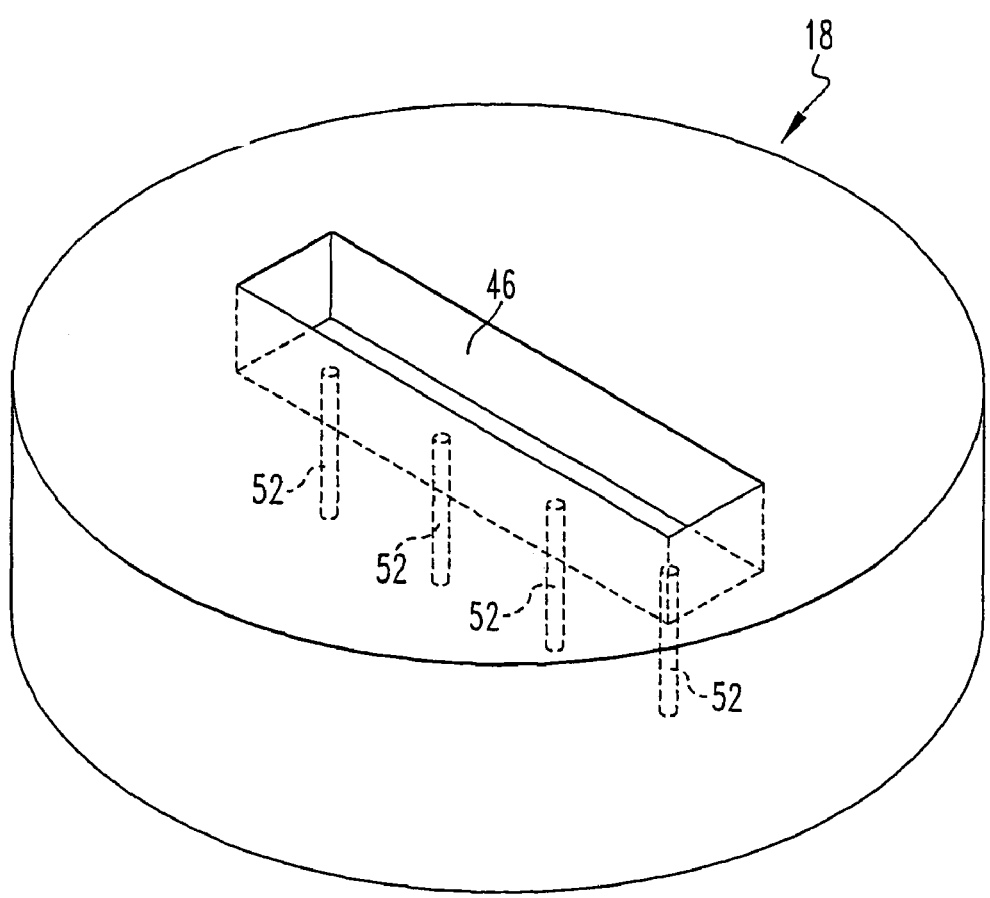
FIG. 6 is a front perspective view of a jig in the apparatus shown in FIG. 1.

Referring to FIGS. 4 and 5, alternatively, the anchor 14' and anchor stem 16' may be annular. One or more members may form the anchor 14'. Likewise, one or more sections may form the anchor stem 16'. For example, the anchor 14' may include four members constructed in quadrants which when potted to the flexible membrane form the annular shape. The anchor stem 16' would be similarly constructed. In this case, the anchor 14' is attached to an outer periphery of the circular flexible membrane 12. In this configuration, the cells are attached in substantially a circle. The cells will intermingle with adjacent cells and grow towards the center and, thereafter, intermingle with other cells at the center to form a continuous construct.

The anchor 14 and/or anchor stem 16 may be constructed from materials such as nylon, silk, cotton, polyester, urethane, or other like materials. The material may be solid and/or mesh. The anchor 14 and/or anchor stem 16 may be a layered series of different materials. The anchor stem 16 may be treated with acidic or basic reagents to improve cell attachment. The anchor stem 16 may be treated further with matrix peptides and/or proteins which are absorbed or covalently bonded to the anchor stem 16.

A tissue segment 36 (see FIG. 10) may be bonded to the anchor stem 16. The tissue segment 36 may be any native tissue, for example, bone, tendon, ligament, muscle, or blood vessel. The cells may then attach to the tissue segment 36 instead of the anchor stem 16. This configuration facilitates the construction of a whole tissue, or a part of a tissue. The tissue segment 36 may include multiple tissues. For example, a bone-ligament-bone graft may be used to grow a construct to replace a damaged anterior cruciate ligament. Also, for example, a bone segment may be bonded to one of the sections 38 or 40 of the anchor stem 16, a muscle segment may be bonded to the other of the sections 38 or 40 of the anchor stem 16, and tendon cells may be used as the supplied cells. Thus, a construct of bone-tendon-muscle may be grown and mechanically conditioned to replace a damaged flexor or extensor tendon in the hand, foot, leg, shoulder, or elsewhere.

Referring now to FIGS. 1–3 and 6, the jig 18 is positioned adjacent the second surface 24 of the flexible membrane 12. The jig 18 may be cylindrical to fit within the well 42 of the culture plate such that the flexible membrane 12 rests on a top surface 44 of the jig 18.

A trough 46 is defined in the jig 18 to be adjacent the second surface 24 of the flexible membrane 12. The trough 46 may be any desired shape to produce a desired shape of structure 34 once the cells adhere to the anchor stem 16. For example, the trough 46 may be shaped to form a structure 34 that is, for example, a rectangle 46, a circle 46' (see FIG. 4), a helix 46" (see FIG. 5), a longitudinal band, a square, a tube, a sphere, or a disc. As specific examples, an elongate band may be used to grow a tendon or ligament, a tube may be used to grow a blood vessel, or a sphere or disc may be used to grow a segment of skin or cornea.

Referring to FIGS. 1 and 3, the means 20 for flexing the flexible membrane 12 preferably includes the well 42 of the culture plate that houses the flexible membrane 12 and jig 18. The well 42 is situated on a gasketed membrane 48, thereby defining a space 50 between the gasketed membrane 48 and the jig 18. The jig 18 includes at least one passage 52, preferably a plurality of passages 52, in fluid communication with the trough 46 and the space 50. The space 50 is also in fluid communication with a vacuum source 54. Vacuum from the vacuum source 54 is applied beneath the jig 18 to aid in forming the cell structure 34 and mechanically conditioning the cells or construct. The means 20 for flexing the flexible membrane 12 may be controlled by a controller 56 (see FIG. 11).

Figure 7:
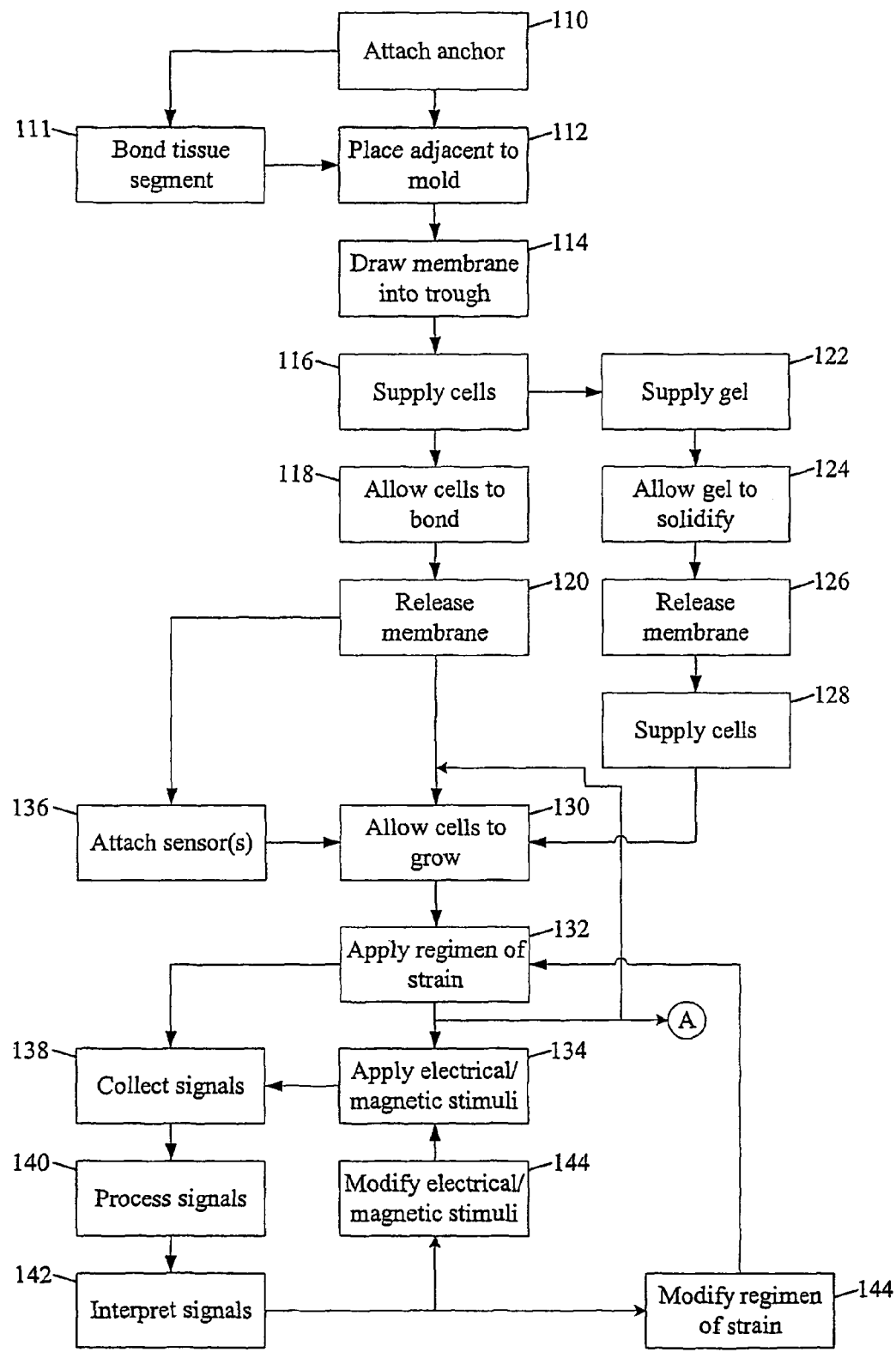
FIG. 7 is a flow diagram illustrating the general method according to the present invention.
Figure 8:
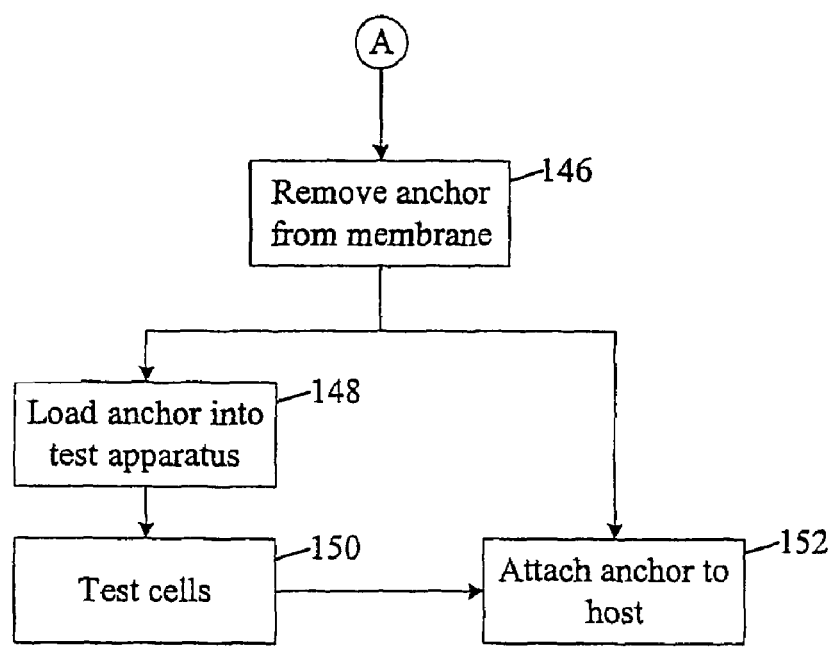
FIG. 8 is a continuation of the flow diagram shown in FIG. 7.
Figure 9:
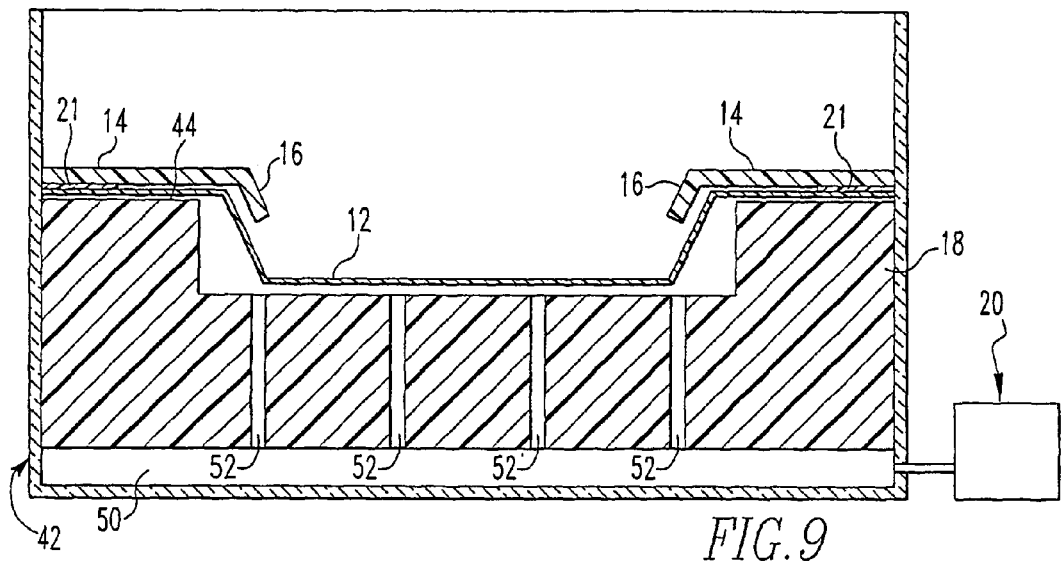
FIG. 9 is a is a section taken along line III—III in FIG. 2 and having a flexible membrane drawn into a trough.

Referring to FIGS. 7 and 8, a method for growing and mechanically conditioning three-dimensional constructs of cell cultures according to the present invention begins by attaching the anchor 14, from which the anchor stem 16 extends, to the first surface 22 of the flexible membrane 12 in step 110. A tissue segment 36 may be bonded to the anchor stem 16 in step 111. The jig 18, having the trough 46 and the at least one passage 52, is placed adjacent the second surface 24 of the flexible membrane 12 in step 112 such that the trough 46 is next to the flexible membrane 12 (see FIG. 3). The flexible membrane 12 and the anchor stem 16 therewith are drawn into the trough 46 in step 114 (see FIG. 9). In step 116, cells are supplied to the flexible membrane 12 where the flexible membrane 12 has been drawn into the trough 46. The cells are allowed to attach to the anchor stem 16, or tissue segment 36, in step 118 (some cells may attach to the flexible membrane 12). Once the cells attach to the anchor stem 16, the flexible membrane 12 is released from within the trough 46 in step 120. The result is a three-dimensional structure 34 of cells that are attached to the anchor stem 16, or tissue segment 36 (see FIG. 10).

In a preferred embodiment, where the means 20 for deforming the flexible membrane 12 includes the vacuum source 54, when vacuum is applied beneath the jig 18, atmosphere is evacuated through the at least one passage 52, and the flexible membrane 12 and the anchor stem 16 deform towards the trough 46 in step 114. When enough vacuum is applied, the flexible membrane 12 is drawn into the trough 46 and assumes a configuration similar to the shape of the trough 46 (see FIG. 9). In this state,. the flexible membrane 12 forms a container suitable to receive the cells in step 116 and hold the cells until they attach to the anchor stem 16 in step 118. The cells may be supplied to the anchor stem 16 at pre-determined locations to form different structures 34. Once the cells create a structure 34 capable of supporting itself in step 118, the vacuum is extinguished in step 120, and the flexible membrane 12 returns to its natural state with the desired three-dimensional structure 34 of cells adhered to the anchor stem 16 (see FIG. 10).

The initial application and duration of the vacuum applied may be varied depending on how long it takes for the cells to attach to the anchor stem 16 in step 118. The duration and level of vacuum introduced to the flexible membrane 12 may be regulated by a Flexercell® Strain Unit (FSU) or like controller device 56. The level of vacuum applied determines how far into the trough 46 the flexible membrane 12 and anchor stem 16 are drawn in step 114. The placement of the at least one passage 52 in the jig 18 defines which area of the flexible membrane 12 is deformed, for example, a passage 52 located near one side of the jig 18 will deform the flexible membrane 12 in that area. The size of the at least one passage 52 helps to define the shape of the structure 34. Thus, the architecture, size, and volume of the three-dimensional cell structure 34 can be regulated.

Cells alone or in a gel matrix may be supplied to the flexible membrane 12 in step 116 to form the three-dimensional cell structure 34. Alternatively, a gel matrix alone may be supplied to the drawn flexible membrane 12 in step 122. When a gel matrix is initially supplied without cells, the gel matrix is allowed to set or at least partially solidify (i.e., polymerize) in step 124 before the flexible membrane 12 is released from within the trough 46 in step 126. Then, cells are supplied to the gel matrix in step 128.

The matrix from any tissue may be used as a starting source for the gel matrix into which cells may be seeded. The gel matrix may be an acid extract of a connective tissue, such as tendon, ligament, skin, bone, cartilage, or other like tissue. Other materials may be used as the gel matrix, including a collagen gel, a polyglycolic acid, a polylactic acid, agarose, alginate, a silicone gel, or a urethane gel.

If an acid extraction is used, then the acid solution may be neutralized with a base so that the final ionic strength is commensurate with cell survival and matrix polymerization into fibrils where desired. When the gel matrix is an acid extract of a connective tissue, the acid composition is preferably 0.5M acetic acid in water; however, other concentrations and acid formulations may be used. Other extraction solutions may be used including salt solutions. The concentration of the matrix solution can be controlled by a user to form a more loose or compact gel.

In step 130, the cells are then allowed to grow to form a three-dimensional construct. Cells populating a gel matrix may reorganize the gel matrix and produce their own matrix, thereby adding to the strength of the matrix. In addition to bonding to the matrix, the cells may also bond directly to the anchor 14 and/or anchor stem 16. In this situation, the cells attach and apply force to the anchor 14 and/or anchor stem 16. In so doing, the cells restructure or remodel the gel matrix, resulting in a construct with greater integrity and strength than if only the gel matrix adhered to the anchor stem 16.

In step 132, while the cells are growing or after the three-dimensional construct has been formed, the flexible membrane 12 is deformed to apply a regimen of strain to the cells or construct attached to the flexible membrane 12. The regimen of strain is applied to the flexible membrane 12 in step 132 to mechanically condition the cells or construct. As with the formation of the cell structure 34, vacuum from the vacuum source 54 is applied beneath the jig 18 to draw the flexible membrane 12 toward the jig 18. The vacuum is extinguished to release the flexible membrane 12 to its original state. The deforming and releasing of the flexible membrane 12 translates to strain applied to the structure or construct (i.e., the cells) attached to the anchor stem 16 on the flexible membrane 12. The strain applied may be static (e.g., deforming and holding the flexible membrane in the deformed state) or cyclic (e.g., repeatedly deforming and releasing the flexible membrane) in order to simulate the strains created by normal activity within a body, for example, during rest or activity. The regimen of strain may be defined, and adjusted, by the user as desired.

To deform the cells or construct with a uniaxial strain regimen, the jig 18 may be an arctangular loading post used in conjunction with the FSU. The face of the arctangular loading post that contacts the second surface 24 of the flexible membrane 12 is a rectangle with the shortest sides curved to fit the dimensions of the overlying flexible membrane 12 (in the culture well 42). The long sides of the arctangular loading post leave a void between the post long sides and the perimeter of the well 42 at opposite poles. When vacuum is applied to the flexible membrane 12, the flexible membrane 12 deforms downward at the two opposing poles. The result is a uniaxial strain applied to the flexible membrane 12 between the two poles which translates into a uniaxial strain applied to the structure or construct (i.e., the cells) attached between the two poles. The surface of the arctangular loading post may be lubricated to facilitate the flexible membrane 12 gliding across the post face.

When an annular anchor 14' and anchor stem 16' are used, a circular loading post is used The circular loading post is of lesser dimension than the flexible membrane 12. In this case, when the vacuum is applied, equibiaxial strain is applied to the cells or construct.

The flexible membrane 12 may be deformed at specific locations to intentionally perturb a nutrifying medium around the structure or construct in order to increase gas exchange, nutrient mixing, and diffusion of medium and gases into the structure or construct (i.e., the cells). This can be achieved by regulating the downward and upward motions of the flexible membrane 12 in a cyclic, intermittent, or continuous fashion. The location of the at least one passage 52 in the jig 18 and the manner in which the vacuum source 54 is connected to the apparatus 10 define the manner in which the flexible membrane 12 is deformed. In this case, a chamber defined by a wall of the well 42, a top (not shown) of the well 42, and the flexible membrane 12 constitutes a bioreactor, with the flexible membrane 12 acting as a valve.

The anchor 14 and/or anchor stem 16 may be constructed of a material (or materials) that allows the passage of electrical signals. Alternatively, an electrically conductive material 58 may be attached to the anchor 14 and/or anchor stem 16 (see FIG. 11). In either case, electrical pulses from a source 60 (see FIG. 11) may be applied to the anchor 14 and/or anchor stem 16 in step 134 and, thereby, to the structure or construct (i.e., the cells) in a regulated fashion. Similarly, magnetic pulses may be applied to the anchor 14 and/or anchor stem 16 in step 134 and, thereby, to the structure or construct (i.e., cells) in a regulated fashion.

Figure 11:
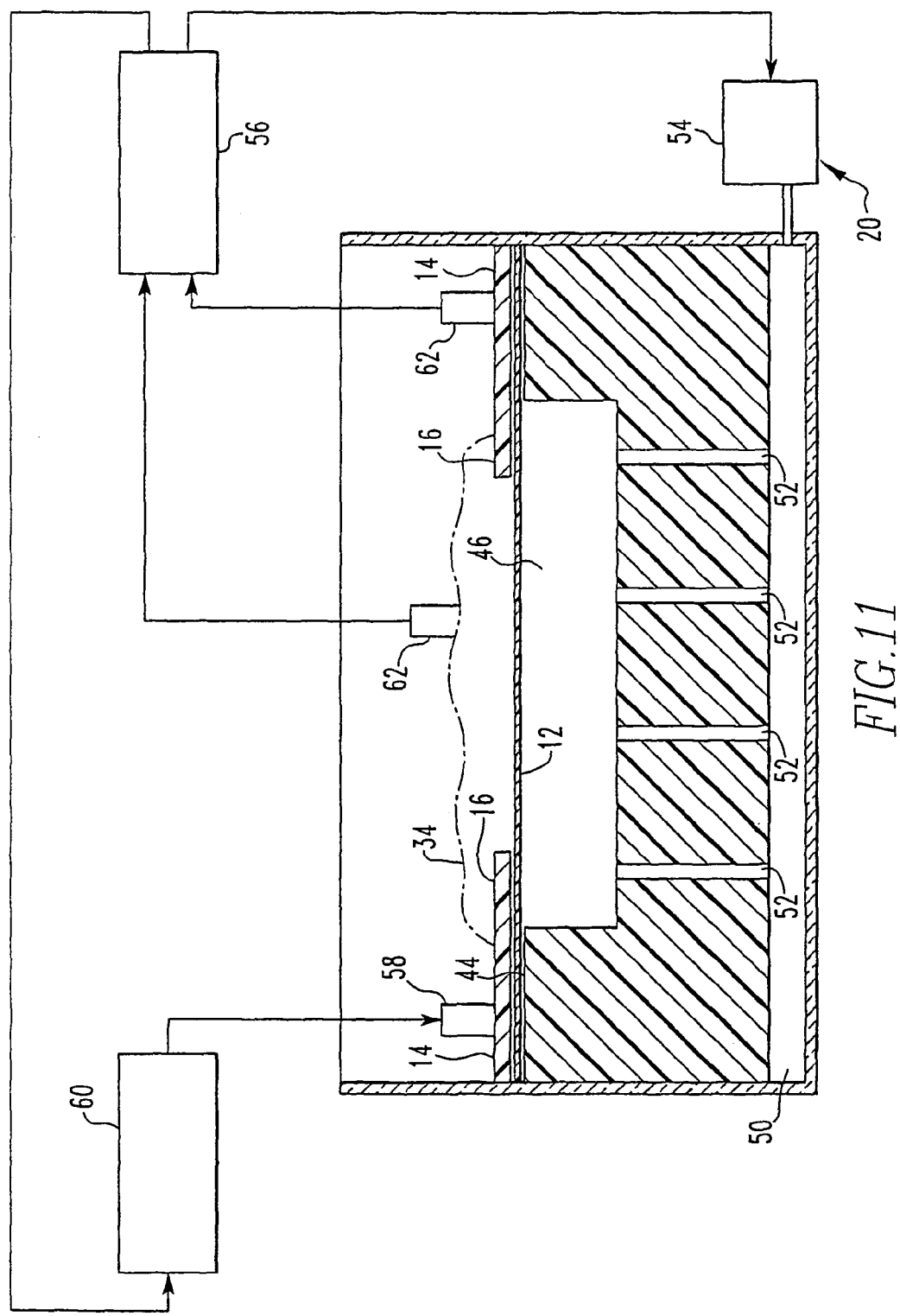
FIG. 11 is a section taken along line III—III in FIG. 2 and showing schematic circuitry.

Sensors 62 may be attached to the anchor 14, anchor stem 16, and/or the structure or construct (i.e., cells) in step 136 (see FIG. 11). Signals from these sensors 62 are collected in step 138 and processed in step 140 by the control device 56, or another device, to monitor the development of the structure or construct (i.e., the cells) (see FIG. 11)—development in the sense that the cells are undergoing metabolic changes and activity, including cell migration and remodeling, structural reorganization, cell division, matrix expression, signal molecule secretion, cell and matrix contraction, electrical pulsation, pH changes, and cell death.

The processed signals may be interpreted in step 142, for example, using a software program. The applied strain (tension, compression, and/or shear), the electrical or magnetic pulses, or the chemistry of the medium surrounding the structure or construct (i.e., the cells) may be adjusted using the control device 56 based on the interpreted processed signals in step 144. This feedback monitoring and regulating of the growth properties help achieve a desired result in the growing cells.

Once the cells in the structure have grown into a suitable construct and have been mechanically conditioned as desired, the anchor 14 may be removed from the flexible membrane 12 in step 146. The anchor 14 may be used to subsequently handle the resulting construct that is attached to the anchor 14 via the anchor stem 16. For example, using the anchor 14, the construct may be loaded into a test apparatus in step 148, such as a tensile or compression load testing device. A test procedure may then be applied to the construct in step 150. As another example, the anchor 14 may be attached into a host in step 152 after removal from the flexible membrane 12 (step 146) or after testing the cells (step 150). In order for the anchor 14 and anchor stem 16 to be fixed into a host, the material of the anchor 14 and anchor stem 16 must be a special resorbable material. This material may be designed to facilitate integration of the construct into the host tissue. Once fixed into the host, the anchor 14 and/or anchor stem 16 may be used as a carrier for further biofeedback control and signal monitoring. For example, the anchor 14 and/or anchor stem 16 may be used as a carrier for matrix molecules, cytokines, growth factors, virus DNA with inserts, plasmid DNA, oligonucleotides, or entire genes for gene transfer that affects the course of development of the construct or surrounding tissue to help achieve integration into the host tissue.

As a specific example, in use, a BioFlex® Culture Plate is placed in a gasketed baseplate attached to an FSU. The FSU provides regulated negative or positive pressure to the baseplate such that the vacuum applied can deform the flexible membrane 12 downward, whereas return to atmospheric pressure releases the flexible membrane 12 to the non-deformed state. The FSU is a microprocessor with software that controls valves and hence controls pressure to the BioFlex® Culture Plate. A program can be set up that allows for active flexing of the flexible membrane 12 in a specific way, so that the growth medium, in which the three-dimensional structure 34 of cells is cultured, is pumped by the action of the flexible membrane 12. The three-dimensional structure 34 of cells is placed in the middle of the medium flow path. As the flexible membrane 12 is drawn downward, the medium flows down and through the matrix. As the flexible membrane 12 travels upward, the fluid flows upward through the matrix. This program can be cycled to a given frequency and amplitude to provide increased nutrient diffusion to cells, as well as mechanical perturbation which may be important to stimulate cell division and matrix expression alone or in synergy with the increased nutrient flow.

It will be understood by those skilled in the art that while the foregoing description sets forth in detail preferred embodiments of the present invention, modifications, additions, and changes might be made thereto without departing from the spirit and scope of the invention.

I claim:

1. A method for growing cell cultures, comprising the steps of:
    attaching an anchor having an anchor stem extending therefrom to a first surface of a flexible membrane;
    placing a jig having a trough adjacent a second surface of the flexible membrane;
    drawing the membrane into the trough in the jig;
    supplying cells to the flexible membrane;
    allowing the cells to attach to the anchor stem;
    releasing the flexible membrane from the trough; and
    allowing the cells to grow.

2. The method according to claim 1, further including the step of applying a regimen of strain to the flexible membrane.

3. The method according to claim 2, further including the step of allowing a user to define the regimen of strain.

4. The method according to claim 2, further including the steps of:
    bonding at least one tissue segment to the anchor stem; and
    allowing the supplied cells to attach to the tissue segment.

5. The method according to claim 2, further including the steps of:
    attaching at least one sensor to the anchor, the anchor stem, and/or the cells;
    collecting signals from the at least one sensor; and
    processing the signals.

6. The method according to claim 5, further including the step of modifying the regimen of strain based on the processed signals.

7. The method according to claim 2, further including the step of applying electrical stimuli to the anchor and/or the anchor stem.

8. The method according to claim 7, further including the steps of:
    applying at least one sensor to the anchor, the anchor stem, and/or the cells;
    collecting signals from the at least one sensor;
    processing the signals; and
    modifying the applied electrical stimuli based on the processed signals.

9. The method according to claim 2, further including the steps of:
    removing the anchor and attached anchor stem and cells from the flexible membrane;
    loading the anchor into a test apparatus; and
    testing the cells.

10. The method according to claim 2, further including the steps of:
    removing the anchor and attached anchor stem and cells from the flexible membrane; and
    attaching the anchor into a host.

11. The method according to claim 2, further including the step of, prior to supplying the cells to the flexible membrane, mixing the cells with a gel matrix.

12. The method according to claim 2, wherein the step of applying the regimen of strain includes the step of deforming the flexible membrane in predetermined locations.

13. A method for growing cell cultures, comprising the steps of:
    attaching an anchor having an anchor stem to a first surface of a flexible membrane;
    placing a jig having a trough adjacent a second surface of the flexible membrane;
    drawing the membrane into the trough in the jig;
    supplying a gel matrix to the flexible membrane;
    allowing the gel matrix to at least partially solidify;
    releasing the flexible membrane from the trough;
    supplying cells to the gel matrix; and
    allowing the cells to grow.

14. The method according to claim 13, further including the step of applying a regimen of strain to the flexible membrane.

15. An apparatus to grow cell cultures, comprising:
    a flexible membrane having a first surface and a second surface;
    an anchor attached to the first surface of the flexible membrane;
    an anchor stem extending from the anchor;
    a jig having a trough positioned adjacent the second surface of the flexible membrane; and
    means for drawing the flexible membrane into the trough and releasing the flexible membrane out of the trough, wherein the flexible membrane is drawn into the jig, cells attach to the anchor stem, and the flexible membrane is released from the jig.

16. The apparatus according to claim 15, wherein:
    the anchor has a first member and a second member, each of the first member and the second member is attached to the flexible membrane, and
    the anchor stem has a first section extending from the first member of the anchor and a second section extending from the second member of the anchor.

17. The apparatus according to claim 16, wherein the first section of the anchor stem is diametrically opposed to the second section of the anchor stem.

18. The apparatus according to claim 15, wherein:
    the anchor is annular and attached to an outer periphery of the flexible membrane, and
    the anchor stem is annular.

19. The apparatus according to claim 15, wherein the means for drawing the membrane into the jig and releasing the flexible membrane out of the jig is a vacuum in fluid communication with at least one passage in the jig which is in fluid communication with the trough.

20. The apparatus according to claim 15, wherein the trough is rectangular.

* * * * *